United States Patent [19]

Bonse et al.

[11] Patent Number: 4,939,262
[45] Date of Patent: Jul. 3, 1990

[54] 6-ETHYL-3-AMINO OR NITRO-2,4-DIHALOGENOPYRIDINE COMPOUNDS

[75] Inventors: Gerhard Bonse, Cologne; Werner Hallenbach, Langenfeld; Hans Lindel, Leverkusen, all of Fed. Rep. of Germany

[73] Assignee: Bayer Aktiengesellschaft, Leverkusen, Fed. Rep. of Germany

[21] Appl. No.: 320,132

[22] Filed: Mar. 7, 1989

[30] Foreign Application Priority Data

Mar. 11, 1988 [DE] Fed. Rep. of Germany ....... 3808115

[51] Int. Cl.$^5$ ............................................. C07D 213/74
[52] U.S. Cl. ..................................... 546/311; 546/312
[58] Field of Search ........................ 546/304, 311, 312

[56] References Cited

FOREIGN PATENT DOCUMENTS

| | | | |
|---|---|---|---|
| 0061588 | 2/1982 | European Pat. Off. ............ | 546/304 |
| 3615293 | 11/1987 | Fed. Rep. of Germany ...... | 546/311 |
| 0040619 | 3/1980 | Japan ................... | 546/309 |
| 0112769 | 6/1985 | Japan ................... | 546/304 |

*Primary Examiner*—Mary C. Lee
*Assistant Examiner*—Zinna Northington-Davis
*Attorney, Agent, or Firm*—Sprung Horn Kramer & Woods

[57] ABSTRACT

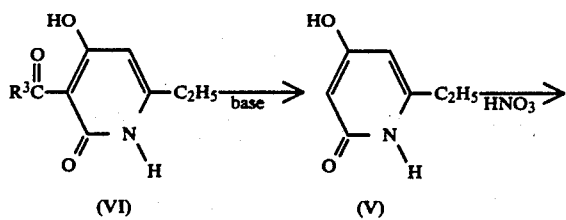

(VI) → (V) →

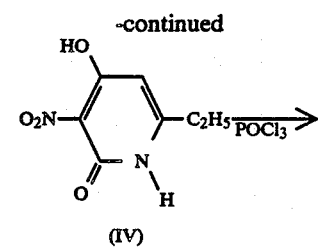

(IV)

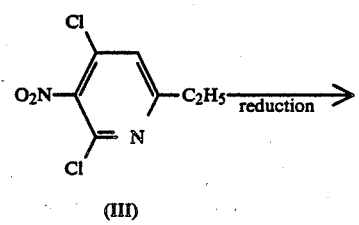

(III)

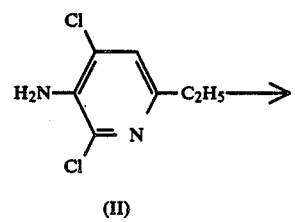

(II)

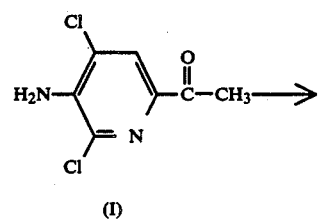

(I)

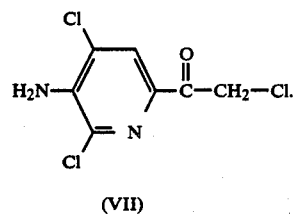

(VII)

(II), (III), (IV) and (V) are new. (VII) is a known intermediate for an animal growth promoter.

2 Claims, No Drawings

6-ETHYL-3-AMINO OR NITRO-2,4-DIHALOGENOPYRIDINE COMPOUNDS

The present invention relates to a process for the preparation of 6-acetyl-3-amino-2,4-dihalogenopyridines and intermediates for their preparation.

6-Acetyl-3-amino-2,4-dihalogenopyridines have been disclosed from (DE-OS (German Published Specification) No. 3,615,293). They are prepared according to the process described there by hydrolysis and decarboxylation of the corresponding pyridylcarbonylacetic acid esters. These are obtained from the corresponding pyridylcarboxylic acid alkyl esters or acid chlorides by reaction with acetic acid esters and a suitable base. The pyridylcarboxylic acid alkyl esters or acid chlorides are prepared from the corresponding pyridylcarboxylic acids.

The pyridylcarboxylic acids are obtained by oxidation of the 6-methyl-3-amino-2,4-dihalogenopyridine. 6-Methyl-3-amino-2,4-dihalogenopyridines are known. In this sequence of reactions it has still not been considered that, for example, an amino substituent of the pyridyl ring must be protected by acetylation before carrying out the reaction on another substituent.

That means, in order to arrive at 6-acetyl-3-amino-2,4-dihalogenopyridine from 6-methyl-3-amino-2,4-dihalogenopyridine, at least four steps are necessary without consideration of the introduction and the elimination of protective groups on the amino substituent. Interest therefore existed in a synthesis for 6-acetyl-3-amino-2,4-dihalogenopyridines which could be carried out more simply.

The present invention relates to:

1. A process for the preparation of 6-acetyl-3-amino-2,4-dihalogenopyridines of the formula I

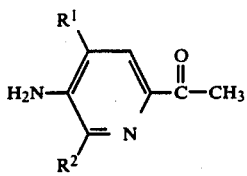

in which
  $R^1$ and $R^2$ stand for halogen, characterized in that 6-ethyl-3-amino-2,4-dihalogenopyridine of the formula II

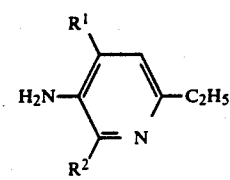

in which
  $R^1$ and $R^2$ have the abovementioned meaning, is first reacted with acylating agents, the compound of the formula II acylated on the amino group is subsequently oxidized using potassium permanganate in a medium maintained at a pH between 4 and 10 and the acyl radical of the amino group is then removed.

2. New 6-ethyl-3-amino-2,4-dihalogeno-pyridines of the formula II

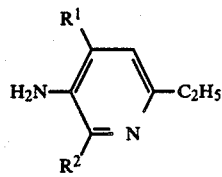

in which
  $R^1$ and $R^2$ stand for halogen.

3. A process for the preparation of 6-ethyl-3-amino-2,4-dihalogenopyridines of the formula II

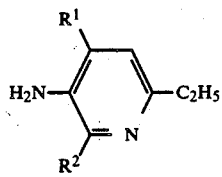

in which
  $R^1$ and $R^2$ stand for halogen, characterized in that 6-ethyl-3-nitro-2,4-dihalogeno-pyridines of the formula III

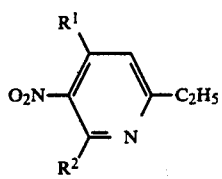

in which
  $R^1$ and $R^2$ have the abovementioned meaning are reduced.

4. New 6-ethyl-3-nitro-2,4-dihalogenopyridines of the formula III

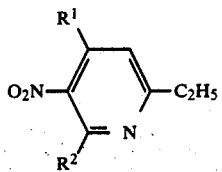

in which
  $R^1$ and $R^2$ stand for halogen.

5. A process for the preparation of the new 6-ethyl-3-nitro-2,4-dihalogeno-pyridines of the formula III according to 4 (above), characerized in that 6-ethyl-3-nitro-4-hydroxy-pyrid-2-one

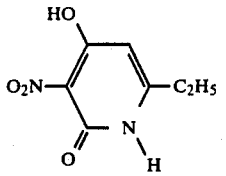

is reacted with phosphorus oxyhalide, if appropriate in the presence of acid-binding agents.

6. 6-Ethyl-3-nitro-4-hydroxy-pyrid-2-one of the formula IV is new.

7. A process for the preparation of 6-ethyl-3-nitro-4-hydroxy-pyrid-2-one, characerized in that 6-ethyl-4-hydroxy-pyrid-2-one is nitrated.

8. 6-Ethyl-4-hydroxy-pyrid-2-one of the formula (V) is new.

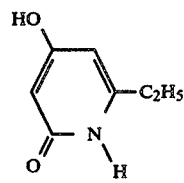   V

9. A process for the preparation of 6-ethyl-4-hydroxy-pyride-2-one, characterized in that 6-ethyl-4-hydroxy-3-carbalkoxypyridines of the formula VI

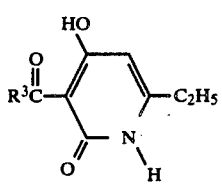   VI in which
R$^3$ stands for OH or C$_{1-3}$-alkoxy, are decarboxylated in the presence of bases.

10. Use of 6-acetyl-3-amino-2,4-dihalogenopyridines of the formula I for the preparation of 6-halogenacetyl-3-amino-2,4-dihalogenopyridines of the formula VII

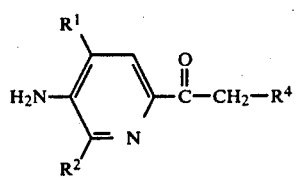   VII in which
R$^1$, R$^2$ and R$^4$ independently of one another stand for halogen,
characterized in that the 6-acetyl-3-amino-2,4-dihalogenopyridines of the formula I are halogenated.

The 6-halogenacetyl-3-amino-2,4-dihalogenopyridines can be converted by reduction of the carbonyl group and subsequent reaction with primary or secondary amines into the corresponding 3-amino-2,4-dihalogeno-pyridylethanolamines. These are used as growth promoters in animals (DE-OS (German Published Specification) 3,615,293). supra.

Preferably, compounds of the formula I, in which R$^1$ and R$^2$ stand for chlorine or bromine, are prepared by process 1.

If 6-ethyl-3-amino-2,4-dichloropyridine is employed as the compound of the formula II in process 1), the individual steps of the process can be represented by the following equations:

Step 1:

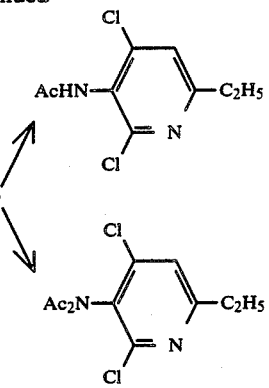

(Ac = Acetyl)

Step 2:

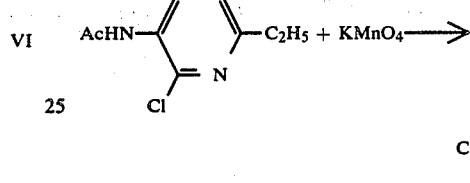

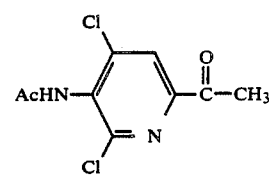

Step 3:

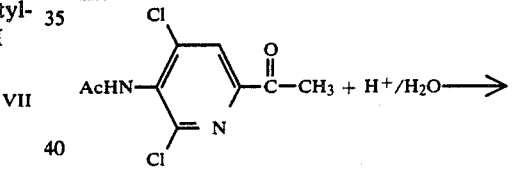

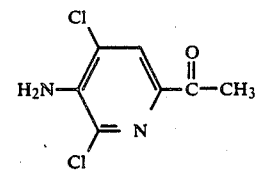

The compounds of the formula II are new. Their preparation is described below.

The acylation of the tirst step takes place using acetic anhydride, acetyl chloride or ketene. The reaction is preferably carried out in the presence of diluents. Those which may be mentioned are all inert organic solvents. In particular, these include aliphatic and aromatic, optionally halogenated hydrocarbons such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers such as diethyl ether and dibutyl ether, glycol dimethyl ether and diglycol dimethyl ether, tetrahydrofuran and dioxane, furthermore ketones such as acetone, methyl ethyl ketone, methyl isopropyl ketone and methyl isobutyl ketone, in addition esters such as methyl acetate and ethyl acetate, furthermore nitriles such as, for example, acetonitrile and propionitrile, benzonitrile, glutaronitrile, and moreover amides such as, for example, dimethylformamide, dimethylacetamide and N-methyl pyrrolidone and also tetramethylene sulphone and hexamethylphosphoric triamide.

The acylation of the first step preferably takes place in the presence of basic catalysts or acylating catalysts. Those which may be mentioned are: for example tertiary amines such as pyridine, 4-dimethylaminopyridine, triethylamine, triethylenediamine, trimethylene-tetrahydropyrimidine; furthermore tin(II) and tin(IV) compounds such as tin(II) octoate or tin(IV) chloride. The tertiary amines mentioned as reaction accelerators, such as, for example, pyridine, can also be used as solvents.

Sodium acetate is particularly preferred.

The reaction is carried out at 0°-250°C., preferably at 50°-150°C. It is carried out at atmospheric pressure.

1-5 moles, preferably 1-2 moles of acylating agent, 1-5 moles, preferably 1-2 moles of basic catalyst and, if appropriate, 0.01-1 mole of acylating catalysts are employed per mole of compound of the formula I.

After completion of the reaction, the reaction mixture is diluted with water and extracted using a water-immiscible solvent. The extracting agent is removed by distillation. A mixture of the mono- or diacetylated compounds of the formula II are thus obtained. This mixture can either be further employed directly or can first be converted into the corresponding monoacetyl compounds by treating with bases in the presence of diluents.

The conversion into the monoacetyl compound takes place in the presence of water, alcohols such as methanol, ethanol, i-propanol, acetone and mixtures thereof.

Bases used are: hydroxides and carbonates of alkali metals and alkaline earth metals, and tertiary amines such as triethanolamine and 4-dimethylaminopyridine.

The reaction is carried out at 0°-150°C., preferably at 10°-100°C. and atmospheric pressure. Water is added to the reaction mixture, it is extracted using a non-polar solvent and the solvent is removed by distillation. The residue is processed further in the second step.

In the second step, the acetylated compound of the formula II is oxidized using potassium permanganate at a pH of 4-10.

The oxidation is carried out in water or mixtures of water with water-miscible organic diluents such as acetone, t-butanol, pyridine, acetonitrile and glycol dimethyl ether.

The pH of the solution is adjusted to 4-10, preferably 5-8, by means of buffer substances.

Buffer substances used are alkali metal dihydrogen phosphates such as sodium dihydrogen phosphate, magnesium nitrate or the mixture from magnesium oxide and nitric acid, magnesium sulphate, calcium sulphate, alkali metal bicarbonates and alkaline earth metal bicarbonates.

The reaction can also be kept in the desired pH range by continuous addition of acids such as, for example, acetic acid.

The oxidation is carried out at temperatures of 0° to 70°C., preferably at 10°-30°C.

1.1-6 moles of potassium permanganate and 1.1-6 moles, preferably 1.1-3 moles, of buffer substance are employed per mole of compound of the formula II.

After completion of the reaction, the $MnO_2$ is filtered off, the solvent is removed by distillation and the mixture is worked up in customary manner.

In the third step, the acetyl group is eliminated in the presence of acids. Acids used are, for example, hydrochloric acid, sulphuric acid, hydrobromic acid, phosphoric acid, methanesulphonic acid, benzenesulphonic acid or strongly acidic ion exchangers.

The reaction is carried out in suitable diluents. Those used are the diluents mentioned for carrying out step 2, for example alcohols such as methanol, ethanol and i-propanol, and ketones such as acetone.

The reaction is carried out at temperatures between 0° and 150°C., preferably 50°-120°C., and at atmospheric pressure.

If 6-ethyl-3-nitro-2,4-dibromopyridine is employed as the compound of the formula III in process (3), the reaction can be represented by the following equation:

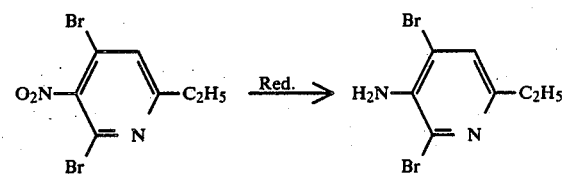

The nitropyridines of the formula III are new. Their preparation is described below in (5).

Reductants used are preferably iron filings, or tin(II) chloride in the presence of an acid.

Acids used are, for example, hydrohalic acids such as hydrochloric acid and hydrobromic acid, or glacial acetic acid. 0.3-10 moles of acid per mole of compound of the formula III are employed. However, the reduction can also be carried out in the acid as diluent.

The reaction can also be carried out in the presence of other diluents. Those used are, for example, alcohols such as methanol, ethanol, butanol, acetic acid, water or mixtures of these diluents.

The reductant is employed in excess. 6-15, preferably 6-9, reducing equivalents of reductants are employed per mole of the compound III.

The reaction is carried out between 0° and 150°C., preferably 50°-120°C.

Working up takes place by filtering the reaction mixture after completion of the reduction, rendering the filtrate alkaline, for example using aqueous sodium hydroxide solution, and extracting the compound of the formula II in a customary manner.

Process (5) can be represented by the following equation:

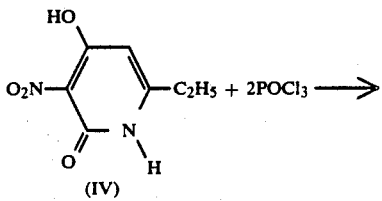

6-Ethyl-3-nitro-4-hydroxy-pyrid-2-one of the formula IV is new. Its preparation is described below.

Process (5) is carried out by treating the compound of the formula IV with 2 to 15 moles, preferably 2 to 4 moles, of the inorganic acid chloride, if appropriate in a diluent.

The reaction is carried out at temperatures of 20°C. to 150°C., and it is preferably carried out at atmospheric pressure.

The reaction can take place in the presence of acid-binding agents. Those which may be preferably mentioned are tertiary organic amines such as, for example, triethylamine, tripropylamine, tributylamine, N,N-dimethylaniline and pyridine.

All inert organic solvents can be used as diluents. In particular, these include aliphatic and aromatic, optionally halogenated hydrocarbons such as pentane, hexane, cyclohexane, benzene, toluene, methylene chloride, chloroform and chlorobenzene; ethers such as diethyl ether, tetrahydrofuran, dioxane, nitriles and esters.

The reaction is preferably carried out without diluents.

Working up takes place in a manner known per se by hydrolyzing the halogenating agent and filtering off the reaction product with suction or removing the solvent by distillation.

Process (7) can be represented by the following equation:

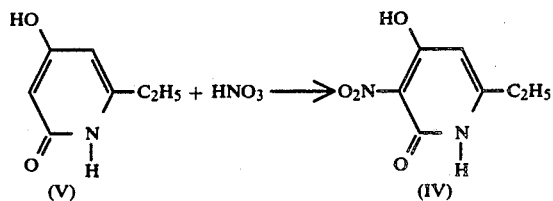

6-Ethyl-4-hydroxy-pyrid-2-one of the formula V is new. Its preparation is described below.

The reaction is carried out in nitric acid or in a mixture of nitric acid and sulphuric acid as nitrating agent At least 1–5 moles of nitrating agent per mole of compound of the formula V are employed.

The reaction is carried out between $-10°$ and 150°C., preferably between 0° and 100°C. and also at atmospheric pressure.

The reaction mixture is diluted with water and the compound of the formula IV is filtered off.

Process (9) can be represented by the following equation:

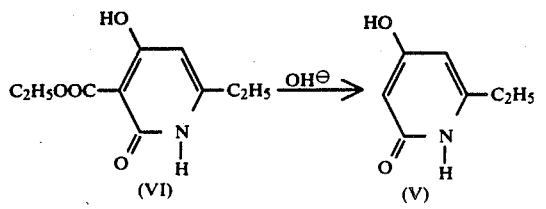

6-Ethyl-4-hydroxy-3-carbalkoxy-pyridines of the formula VI are new. Compounds of the formula VI are preferred in which $R^3$ stands for methyl or ethyl.

Decarboxylation to compounds of the formula V is carried out in the presence of aqueous bases such as alkali metal hydroxides or alkaline earth metal hydroxides. 2–10, preferably 2–5, moles of base per mole of compound of the formula VI are employed. The reaction is carried out between 20° and 200°C., preferably between 50° and 150°C.

After completion of the reaction, the mixture is made weakly acidic and the compound of the formula V is filtered off.

The compounds of the formula VI can be prepared by reacting enamines of the formula VIII

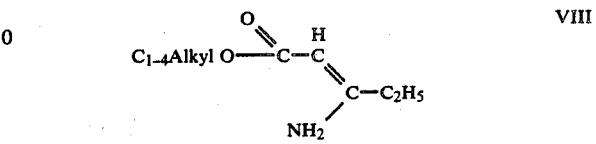

in which
$C_{1-4}$-alkyl preferably stands for methyl or ethyl, with malonates of the formula IX

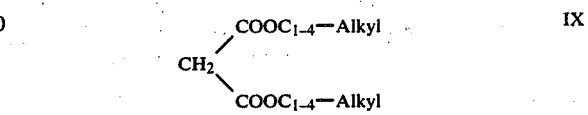

in which
$C_{1-4}$-alkyl preferably stands for methyl or ethyl, in the presence of bases.

The compounds of the formula VIII and IX are employed in a molar ratio of about 1:1.

Bases used are alkali metal alkoxides and alkaline earth metal alkoxides such as sodium methoxide or potassium t-butoxide.

The bases are employed in a ratio of 1:3, preferably 1:1.5, per mole of malonate.

Diluents used are alcohols such as methanol, ethanol, i-propanol, t-butanol and also inert organic solvents, in particular aliphatic and aromatic, optionally halogenated hydrocarbons such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, furthermore ethers such as diethyl ether and dibutyl ether, glycol dimethyl ether and diglycol dimethyl ether, tetrahydrofuran and dioxane, moreover amides such as, for example, dimethylformamide, dimethylacetamide and N-methylpyrrolidone and also dimethyl sulphoxide, tetramethylene sulphone and hexamethylphosphoric triamide.

As already mentioned (10), the 6-acetyl-3-amino-2,4-dihalogenopyridines of the formula I can be used in order to prepare pyridinethanolamines.

The reaction steps passed through in the course of this can be represented by the following equation:

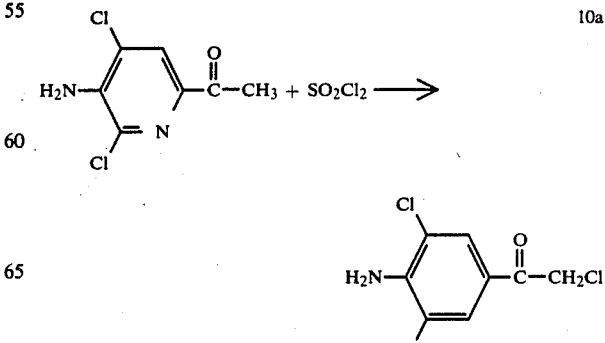

-continued

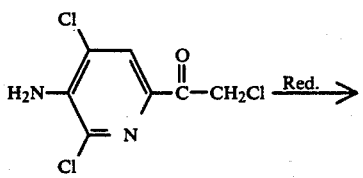

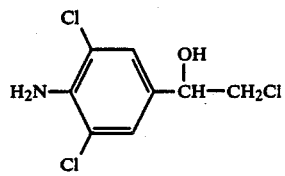

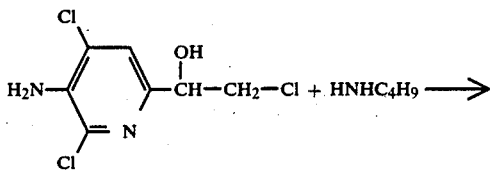

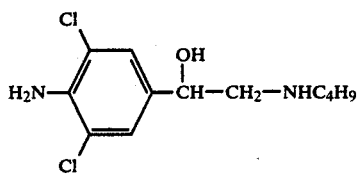

Sulphuryl chloride is preferably employed as a halogenating agent in reaction step 10a.

1-3, preferably 1-1.5, moles of halogenating agent are employed per mole of compound of the formula I.

The reaction is carried out in the presence of diluents. Those which may be mentioned are aliphatic, optionally halogenated hydrocarbons such as, for example, pentane, hexane, heptane, ligroin, cyclohexane, methylene chloride, ethylene chloride, chloroform, carbon tetrachloride, alcohols such as methanol and ethanol, esters such as methyl acetate or ethyl acetate and mixtures of these diluents.

The reaction is carried out between $-20°$ and $+150°$ C., preferably between $0°$ and $70°$ C., and at atmospheric pressure.

Reaction step 10b is preferably carried out using the reductants diborane or complex hydrides such as, for example, sodium borohydride or lithium borohydride.

In step 10c, the following amines are preferably employed: ammonia, methylamine, i-propylamine, i-butylamine, sec.-butylamine, tert.-butylamine, cyclopentylamine, cyclohexylamine, 1-cyclohexylethylamine, benzyl-amine, 2-phenylethylamine and 2-phenyl-propylamine.

Step 10 can be carried out with or without diluents. Diluents which may be mentioned are: in particular, aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene; furthermore ethers such as diethyl ether and dibutyl ether, glycol dimethyl ether and diglycol dimethyl ether, tetrahydrofuran and dioxane; furthermore nitriles, such as, for example, acetonitrile and propionitrile, benzonitrile, and glutaronitrile: moreover amides, such as, for example, dimethylformamide, dimethylacetamide and N-methylpyrrolidone; and also dimethyl sulphoxide, tetramethylene sulphone and hexamethylphosphoric triamide.

Step 10c can be carried out in the presence of catalysts such as, for example, alkali halides, for example sodium bromide, potassium iodide, quaternary ammonium iodides or quaternary ammonium bromides.

The reaction is carried out at temperatures of $25°-250°$ C., preferably $50°-150°$ C.

The reaction is carried out at atmospheric pressure or under elevated pressure.

2-10 moles, preferably 2-3 moles, of amine are employed per mole of halogenoethanolpyridine.

Working up after completion of the reaction takes place in a manner known per se.

EXAMPLE 1 (Process 1 (Step 1))

3-Acetamido-2,4-dichloro-6-ethylpyridine 7.8 g (40.8 mmol) of 3-amino-2,4-dichloro-6-ethylpyridine are heated under reflux for two hours in a mixture of 40 ml of acetic anhydride and 4 g (49 mmol) of anhydrous sodium acetate. The mixture is subsequently evaporated in vacuo, the residue is partitioned between dilute $NH_3$ solution and $CHCl_3$, and the organic phase is separated off, dried using $Na_2SO_4$ and evaporated. The residue (11.2 g) consists of a mixture of mono- and diacetylated amine. It is dissolved in 50 ml of methanol, 10 g of powdered $K_2CO_3$ are added and the mixture is stirred for one hour at room temperature. It is subsequently evaporated and partitioned between water and $CHCl_3$, and the organic phase is separated off and washed with 5% strength aqueous $NaH_2PO_4$ solution. After drying using $Na_2SO_4$, the organic phase is evaporated. The residue is stirred with ether and filtered off with suction. Yield 7.7 g (80.9% of theory) melting point: 142° C.

EXAMPLE 2 (Process 1 (Step 2))

6-Acetyl-3-acetamido-2,4-dichloropyridine 125.7 g (0.49 mol) of $Mg(NO_3)_2 \cdot 6H_2O$ are initially introduced into a 3 l three-necked flask and dissolved in 410 ml of water. 34.4 g (0.15 mol) of 3-acetamido-2,4-dichloro-6-ethylpyridine, dissolved in 410 ml of acetone, and a further 370 ml of water and 55.5 g (0.35 mol) of $KMnO_4$ are subsequently added. The mixture is stirred at 26° C. for 18 hours. The precipitate is then filtered off with suction and the filter cake is carefully washed with acetone. The filtrate is evaporated and partitioned between dichloromethane and water. The organic phase is separated off, dried using $Na_2SO_4$ and evaporated. Yield: 24.5 g, melting point: 133°-7° C. Purity by GC/MS: 41% product 58% starting material.

EXAMPLE 3 (Process 1 (Step 3))

3-Amino-6-acetyl-2,4-dichloropyridine 43.3 g of a mixture of 41% of 6-acetyl-3-acetamido-2,4-dichloropyridine and 59% of 3-acetamido-2,4-dichloro-6-ethylpyridine are dissolved in 345 ml of methanol and 172.4 ml of 36% strength aqueous HCl are then added. The mixture is heated under reflux for 2½ hours.

900 ml of water are subsequently added, and the mixture is cooled using an ice bath. The precipitate is filtered off with suction and washed with water.

Yield: 14.47 g (98% of theory calculated on the purity of the starting material employed). Melting point: 162° C.

The filtrate is rendered alkaline using sod hydroxide solution and extracted using dichloromethane. After evaporating, 20 g (95.5% of theory based on the purity of the starting material employed) of 3-amino2,4-dichloro-6-ethylpyridine remain.

EXAMPLE 4 (Process 3)

3-Amino-2,4-dichloro-6-ethylpyridine 9 g (40.7 mmol) of 2,4-dichloro-6-ethyl-3-nitropyridine are introduced into a solution of 33 g (0.146 mol) of $SnCl_2 \cdot 2H_2O$ in 100 ml of 36% strength HCl and the mixture is boiled under reflux for 30 minutes. It is then cooled and stirred into 400 ml of 12% strength NaOH with cooling. It is extracted three times using 150 ml of dichloromethane each time and the extract is dried using $Na_2SO_4$ and evaporated.

Yield: 7.8 g (quantitative).

EXAMPLE 5 (Process 5)

2,4-Dichloro-6-ethyl-3-nitropyridine 58 g (0.315 mol) of 6-ethyl-4-hydroxy-3-nitro-1H-2-pyridone are introduced into 500 ml of $POCl_3$ and the mixture is stirred for 16 hours at 77° C. It is subsequently evaporated in vacuo, and the residue is hydrolyzed using ice, neutralized using NaOH and extracted three times using 300 ml of $CHCl_3$ each time. The extract is washed with 5% strength $NaH_2PO_4$ solution, dried using $Na_2SO_4$ and evaporated. The residue is filtered over silica gel using dichloromethane.

Yield: 47 g (67.5% of theory) of yellow oil.

EXAMPLE 6 (Process 7)

6-Ethyl-4-hydroxy-3-nitro-1-H-2-pyridone 20 g (0.145 mol) of 6-ethyl-4-hydroxy-1-H-2pyridone are suspended in 60 ml of 65% strength $HNO_3$ and heated to 65° C. The strongly exothermic reaction is kept under control by cooling with ice. After the reaction subsides, 120 ml of water are added and the mixture is cooled with ice. After 30 minutes, the precipitate is filtered off with suction and dried.

Yield: 13.7 g (51% of theory).
Melting point: 185°C.

EXAMPLE 7 (Process 9)

6-Ethyl-4-hydroxy-1H-2-pyridone 119 g (0.564 mol) of 3-carbethoxy-6-ethyl-4-hydroxy-1H-2-pyridone are heated under reflux for two hours in a mixture of 1l of water with 155 g (2.77 mol) of KOH. After cooling, the mixture is adjusted to pH 4 using concentrated HCl, cooled again and filtered with suction.

Yield: 74.7 g (95% of theory). Melting point: 274° C.

EXAMPLE 8 (Preparation of the compounds of the formula VI)

3-Carbethoxy-6-ethyl-4-hydroxy-1H-2-pyridone 113.6 g (0.88 mol) of methyl 3-amino-2-pentenoate and 128 g (0.8 mol) of diethyl malonate are added to a solution of 259.2 g (0.8 mol) of 21% strength sodium methoxide solution in methanol and 130 g of ethanol. After addition of 800 ml of 1,2-dichlorobenzene, a mixture of methanol and ethanol is removed by distillation in the course of one hour and the remaining suspension is heated to 160° C. for two hours. After cooling, 600 ml of water are added, and the organic phase is separated off, extracted using water and then discarded. The combined aqueous phases are washed with ether, and the aqueous phase is separated off, acidified using hydrochloric acid and filtered off with suction.

Yield: 118.9 g (70.5% of theory).
Melting point: 189° C.

EXAMPLE 9 (Process 10 (Step a))

3-Amino-6-chloroacetyl-2,4-dichloropyridine 14 g (68.3 mmol) of 6-acetyl-3-amino-2,4-dichloropyridine are dissolved in 70 ml of dry $CHCl_3$ and then a solution of 5.5 ml (68.4 mmol) of $SO_2Cl_2$ in 70 ml of dry $CHCl_3$ is added dropwise and the mixture is stirred for two hours at 40° C. For working up, it is poured into 250 ml of $NaHCO_3$ solution, and the organic phase is separated off and extracted once more using 100 ml of $CHCl_3$. The combined organic phases are dried using $Na_2SO_4$ and evaporated.

Yield: 16 g, not further purified.
Melting point: 142°–4° C.

EXAMPLE 10 (Process 10 (Step b))

2-Chloro-1-(3-amino-2,4-dichloro-6-pyridyl-ethanol 16 g (66.8 mmol) of 3-amino-6-chloroacetyl-2,4-dichloropyridine are suspended in 150 ml of methanol and cooled to 0° C., and 2.78 g (73.5 mmol) of $NaBH_4$ are introduced. The mixture is stirred for 15 minutes at 0° C., then poured into 300 ml of 5% strength $NaH_2PO_4$ solution and stirred for 15 minutes. It is then exhaustively extracted with $CHCl_3$. After drying using $Na_2SO_4$, the extract is evaporated and chromatographed over silica gel using $CH_2Cl_2$/ethyl acetate as an eluent for purification.

Yield: 13.1 g (81% of theory).
Melting point: 74° C.

EXAMPLE 11 (Process 10 Step c))

2-N-tert.-Butylamino-1-(3-amino-2,4-dichloro-6-pyridylethanol 3 g (12.4 mmol) of 2-chloro-1-(3-amino-2,4-dichloro-6-pyridyl)-ethanol and 60 mg of tetrabutylammonium iodide are heated to 100° C. for 12 hours together with 24 ml of tert.-butylamine. For working up, the mixture is evaporated, and the residue is partitioned between 200 ml of 5% strength $NaH_2PO_4$ solution and 200 ml of ether. The organic phase is discarded, and the aqueous phase is rendered alkaline using NaOH and extracted using dichloromethane. After drying using $Na_2SO_4$, the extract is evaporated, the residue is dissolved in 10 ml of ether and petroleum ether is added to slight turbidity. To complete the crystallization, the solution is allowed to stand overnight and the precipitate is then filtered off with suction and washed with petroleum ether.

Yield: 1 g (30% of theory).
Melting point: 124° C.

It will be appreciated that the instant specification and claims are set forth by way of illustration and not limitation, and that various modifications and changes may be made without departing from the spirit and scope of the present invention.

What is claimed is:

1. A b 6-ethyl-3-amino-2,4-dihalogeno-pyridine of the formula

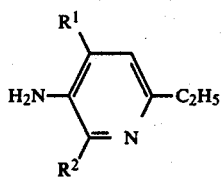
in which
R¹ and R² each is halogen.
2. A 6-ethyl-3-nitro-2,4-dihalogenopyridine of the formula
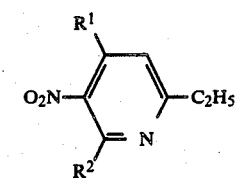
in which
R¹ and R² each is halogen.

UNITED STATES PATENT AND TRADEMARK OFFICE
CERTIFICATE OF CORRECTION

PATENT NO. : 4,939,262

DATED : July 3, 1990

INVENTOR(S) : Gerhard Bonse, et al

It is certified that error appears in the above-identified patent and that said Letters Patent is hereby corrected as shown below:

Col. 12, line 67          After "A" delete "b"

Signed and Sealed this

Twenty-third Day of March, 1993

Attest:

STEPHEN G. KUNIN

*Attesting Officer*     *Acting Commissioner of Patents and Trademarks*